United States Patent [19]

Castel et al.

[11] 4,453,547

[45] Jun. 12, 1984

[54] T-WAVE INHIBITING SYSTEM

[75] Inventors: John C. Castel, Lake Bluff; Richard G. Kerwin, Prospect Heights, both of Ill.

[73] Assignee: Physio Technology, Inc., Topeka, Kans.

[21] Appl. No.: 251,139

[22] Filed: Apr. 6, 1981

[51] Int. Cl.³ .............................................. A61N 1/36
[52] U.S. Cl. ................................ 128/421; 128/423 R; 128/908
[58] Field of Search ........... 128/419 R, 419 C, 419 E, 128/419 S, 420 R, 421, 422, 423 R, 908

[56] References Cited

U.S. PATENT DOCUMENTS

| | | | |
|---|---|---|---|
| 3,129,704 | 4/1964 | Burt, Jr. ....................... | 128/419 R X |
| 3,478,746 | 11/1969 | Greatbatch .......................... | 128/421 |
| 3,566,876 | 3/1971 | Stoft et al. ........................ | 128/421 |
| 3,628,538 | 12/1971 | Vincent et al. ...................... | 128/422 |
| 3,650,277 | 3/1972 | Sjostrand ........................ | 128/421 X |
| 3,747,604 | 7/1973 | Berkovitz ........................ | 128/419 P |
| 3,814,106 | 6/1974 | Berkovitz ........................ | 128/419 P |
| 3,946,745 | 3/1976 | Hsiang-Lai et al. ................ | 128/421 |
| 4,084,595 | 4/1978 | Miller ................................. | 128/422 |
| 4,088,141 | 5/1978 | Niemi ................................. | 128/421 |

Primary Examiner—Lee S. Cohen
Attorney, Agent, or Firm—Wood, Dalton, Phillips, Mason & Rowe

[57] ABSTRACT

An electrical inhibitor system is disclosed for suppressing the application of transcutaneous nerve stimulator (TNS) signals during the T-wave portion of a heartbeat. The system includes a sensing circuit which is coupled to detect the R-S waveform produced by the heart during its normal beating pattern. Upon detection of the R-S portion of the waveform, an electrical signal is produced and coupled to timing circuitry to produce a timing signal having a duration in excess of the normal period of the T-wave portion of the heartbeat. The timing signal is to inhibit the output of a transcutaneous nerve stimulator during the T-wave portion of the heartbeat. When the inhibiting circuit and transcutaneous nerve stimulator are coupled to a patient, the system provides an inhibiting signal beginning during the R-S portion of the waveform and extending through the T-wave portion of the hearbeat to prevent application of the output from the transcutaneous nerve stimulator during the vulnerable period of the heart. The transcutaneous nerve stimulator can thus be used without endangering the patient from electrical stimulation.

8 Claims, 8 Drawing Figures

FIG.1
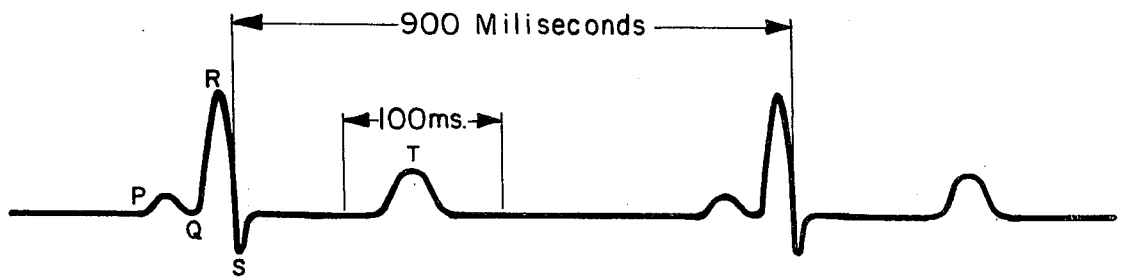
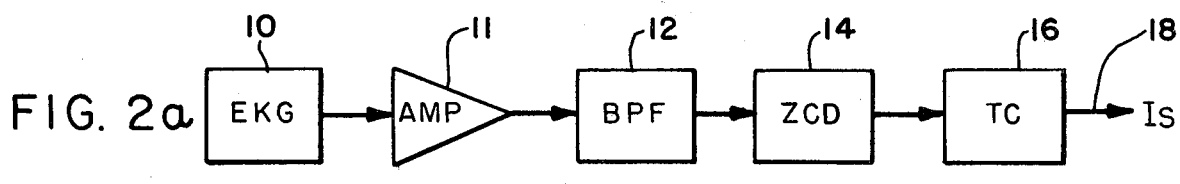
FIG. 2a
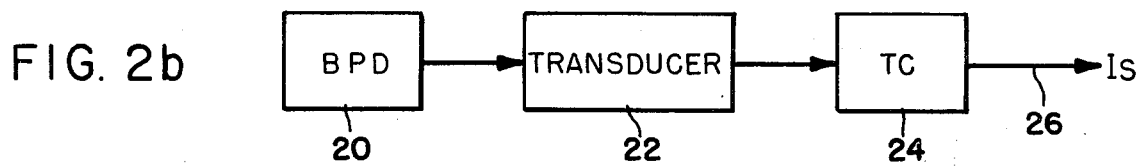
FIG. 2b
FIG.3
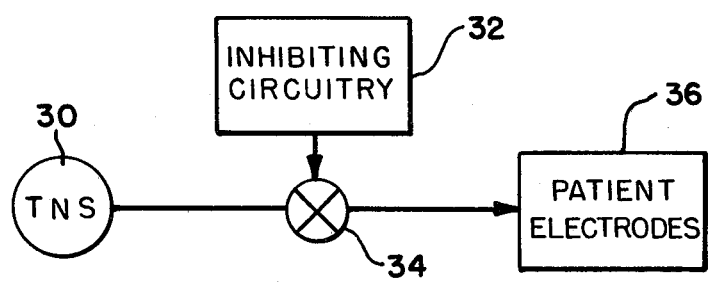

T-WAVE INHIBITING SYSTEM

BACKGROUND OF THE INVENTION

The present invention relates to electrical stimulating devices for application to the human body and, more particularly, to transcutaneous nerve stimulator systems for providing external electrical signals for body stimulation and treatment.

Transcutaneous nerve stimulating circuits are conventionally used in the prior art to provide patient treatment by applying electrical stimulation externally to the body for treatment of pain and muscular problems. The technique involves the application of electrical impulses to various parts of the body at different magnitudes and durations. The impulses are provided by conventional pulse-producing circuitry which produces pulses of various magnitudes and durations and a variety of timing intervals. The pulses are coupled through electrodes which are attached to the skin of a patient for coupling to the body.

While the application of the transcutaneous nerve stimulations has been a long-standing practice, and has appeared to provide various degrees of relief from pain and other muscle problems, the technique and the devices used to produce the electrical impulses pose a danger to an individual because of the electrical pulses being used. This danger is related to the normal heart function and beat pattern of the heart in the body. As is known, the typical heartbeat waveform is repetitive and consists of specific periods generally known as the P, Q, R, S, and T portions of the heartbeat. Each of the individual portions are known by the respective capital letters as the particular wave portion of the heartbeat. The time duration of each of the periods is generally well-known and the whole time period from the beginning of one heartbeat period to the beginning of the next heartbeat period is generally about 900 milliseconds. Of this 900 millisecond period, the T-wave portion lasts approximately 100 milliseconds and is considered the vulnerable period of the heartbeat.

The T-wave portion is considered the vulnerable period because of the tendency of the heat to go into ventricular fibrillation if it is electrically stimulated during that period. Ventriclar fibrillation is a state in which the heart does not beat properly and prevents proper operation of the heart valves to control blood flow through the body. When blood flow is lost, oxygen and other nutrients required by the heart and other portions of the body are not provided because of lack of blood flow, and serious injury can result. Because the heart is susceptible to electrical stimulation during the T-wave portion, it is necessary to take great care to prevent electrical stimulation to or around the heart during that time period.

During the use of transcutaneous nerve stimulators, the application of unwanted electrical signals can be prevented by localizing the treatment away from the heart. This technique still poses a problem, however, because of uncontrolled electrical paths during body stimulation. While the electrodes may be positioned to provide the stimulation to a particular area, some portion of the energy provided to the electrodes can be passed to other parts of the body where no stimulation is required or desired. If this were to happen to the heart during the T-wave portion of the heartbeat, the stimulation could cause the unnatural interruption of the heartbeat.

In the prior art, the problem has been reduced to some degree by reducing the magnitude of the nerve stimulation pulses below a level at which the heart would be disrupted if any electrical stimulation is received during the T-wave portion. In addition, the electrodes are usually applied to parts far from the heart to avoid inadvertent stimulation of the heart muscle. While this technique may be successful in eliminating most of the danger, it also reduces the effectiveness of transcutaneous nerve stimulation since greater magnitude pulses than safety dictates are required for the proper treatment of the body portions.

There is thus a need for a transcutaneous nerve stimulation system which will enable the application of greater magnitude pulses while reducing the danger of inadvertent electrical stimulation of the heart. The present invention has therefore been developed to overcome the shortcomings of the above known and similar systems and techniques and to provide a transcutaneous nerve stimulation and inhibiting system for inhibiting electrical signals during the T-wave portion of the heartbeat.

SUMMARY OF THE INVENTION

The present invention includes a transcutaneous nerve stimulator (TNS) circuit coupled to a T-wave inhibiting circuit to produce a transcutaneous nerve stimulation output which is inhibited during the T-wave portion of the heartbeat. The T-wave portion of the heartbeat is detected by a sensing circuit coupled to the body of the person to be stimulated. The sensing circuit can include an EKG which detects electrical signals representing the heartbeat directly from the body to produce a timing signal or a blood pressure detector which is coupled to a converting circuit and produces an electrical signal for initiating the timing signal. In either case, the R-S portion of the heartbeat is detected and a timing signal produced which extends beyond the normal T-wave portion of the heartbeat. This signal is coupled through appropriate circuitry with the output of a transcutaneous nerve stimulating circuit. When the signals are combined, the timing signal prevents the output of the transcutaneous nerve stimulator circuit from reaching the electrodes attached to the body of a patient during the T-wave portion of the heartbeat. When the system is connected to the body to provide electrical nerve stimulation, the magnitude can be increased to the appropriate levels without the danger of interruption of the heart or stimulation of the heart during the vulernable period.

It is therefore a feature of the invention to provide a transcutaneous nerve stimulation system which is of less danger to the patient.

It is another feature of the invention to provide transcutaneous nerve stimulation which is inhibited during the T-wave portion of the heartbeat.

It is a further feature of the invention to detect the R-S portion of the heartbeat and provide a timing signal which extends to the end of the T-wave portion of the heartbeat.

Still another feature of the invention is to provide a timing signal coupled to the output of a transcutaneous nerve stimulating circuit to inhibit that output during the presence of the timing signal.

Yet another feature of the invention is to provide a transcutaneous nerve stimulation and inhibiting system which provides a nerve stimulating output to the body and which is suppressed by an inhibiting signal detected from the body to prevent electrical stimulation of the heart during the vulnerable period.

These and other novel features of the present invention will become apparent from the following detailed description of the invention when taken with the accompanying drawings wherein:

BRIEF DESCRIPTION OF THE DRAWINGS

FIG. 1 is a diagram of a typical waveform of the heart showing the normal beating waveform portions and repitition periods.

FIG. 2a is a block diagram showing a detection circuit using an EKG for producing an inhibiting signal.

FIG. 2b is a block diagram showing a detection circuit using a blood pressure transducer for producing an inhibiting signal.

FIG. 3 is a block diagram showing the transcutaneous nerve stimulation and inhibiting system of the present invention.

FIG. 4b is a diagram of the typical heartbeat waveform in time relation to the transcutaneous nerve stimulator waveform of FIG. 4a.

DETAILED DESCRIPTION OF A PREFERRED EMBODIMENT

Figure 4A:
FIG. 4a is a diagram of the waveform produced by a typical transcutaneous nerve stimulator.

Turning first to FIG. 1 there is shown a schematic diagram of a typical repetitive heartbeat waveform. The waveform consists of several major amplitude portions which are labeled P, Q, R, S, and T and are generally known as conventional heartbeat phases to those knowledgeable in the art. The repitition rate of a typical heartbeat will vary depending upon the circumstances but may generally be approximately 900 milliseconds. If the heart is functioning properly, the waveform will repeat regularly during a particular time period.

As has been noted previously, the T-wave portion of the heartbeat is considered to be the vulnerable period of the heart function. It is during this time that various problems can be triggered if the heart is subject to outside electrical stimulation. While the period generally only lasts approximately 100 milliseconds of the heartbeat, this time period is critical if it is necessary to subject a person to electrical stimulation. Because of the vulnerability, various institutions have adopted a policy which prohibits the use of any apparatus which is to be directly connected to any individual if its output current exceeds 10 to 20 microamperes, the figure at which the heart may be affected. Other institutions have adopted a policy that even if the equipment is not to be connected to an individual, its output current must be limited to the range of 200 to 550 microamperes where it would be used in proximity to individuals. While these limits are not standard, they do substantially affect the type of equipment that may be used in institutions that are treating individuals.

In the area of transcutaneous nerve stimulation, there are a variety of devices which can be used for treatment of individuals. While the circuitry is not important to this particular inventive system, the transcutaneous nerve stimulators are designed to provide a series of repetitive pulses which may be varied in amplitude, duration and period of repetition. The pulses are used in the treatment of pain by supplying them to the body of an individual through electrodes attached in proximity to the treating area. When attached, the electrodes deliver the pulses to the area located between them and thus provide the stimulation necessary for the particular treatment involved.

While the devices used in the prior art are designed to provide the localized supply of electrical stimulation, there is always an inherent danger that electrical impulses delivered to one part of the body will have an effect in another part of the body. In particular, there is always the danger that the electrical impulses being delivered by a transcutaneous nerve stimulator will undesirably stimulate the heart during the vulnerable T-wave portion, causing disruptions in the heart function. Since the levels that successful transcutaneous nerve stimulators must be operated are far in excess of that required to cause adverse effects in the heart function, there is a strong need to guard against the application of electrical stimulation to the heart during the T-wave portion.

In accordance with the present invention, therefore, a transcutaneous nerve stimulation inhibiting system has been developed which includes sensors to detect the repetitive heart waveform and provide a timing signal extending through the T-wave portion of the heartbeat. Referring specifically to FIG. 2a, there is shown a sensing circuit which detects the electrical signals provided by the heart in a manner similar to the operation of an EKG. In this instance, the electrical signals produced in the heart are detected directly from the body of an individual by electrodes placed on the skin. These signals are provided as an EKG output at element 10 in the diagram. These electrical signals are then passed to an amplifier 11 and filtered with a conventional filter 12. The output from filter 12 will be a filtered version of the R-S portion of the heartbeat. This output is coupled to a zero crossing detector 14 which senses the change in amplitude from the positive R portion of the heartbeat waveform to the negative S portion of the heartbeat waveform to give an output signal when the transition occurs.

At this time, the zero crossing detector 14 produces a pulse which is provided to a timing circuit 16. The timing circuit 16 can be any conventional circuit designed to provide an output pulse of a fixed duration upon receipt of an input pulse from the zero crossing detector 14. The output of the timing circuit is provided as an output inhibiting signal from lead 18 in FIG. 2a.

As an alternative to the embodiment of FIG. 2a, the inhibiting signal can be developed directly from the sensing of an individual's blood pressure. In FIG. 2b, for example, a pressure transducer 20 can be attached to the body of an individual to give a reading of the blood pressure as the heart beats. Since it is known that blood pressure variations are substantially synchronous with the heartbeat waveform shown in FIG. 1, the blood pressure reading can be used to create an electrical signal corresponding to the transition between the R-S portion of the heartbeat. Typically, the blood pressure transducer can be coupled to a pressure-to-electrical transducer 22 which creates an electrical output pulse upon receiving a predetermined output from the blood pressure transducer. The electrical signal from transducer 22 is then supplied to a timing circuit 24 which operates in a manner similar to timing circuit 16 to provide a pulse output on the line 26 having a predetermined duration subsequent to the receipt of a signal from transducer 22.

The inhibiting signal 18, indicating the duration of the T-wave portion, can be produced by either of the circuits of FIG. 2a or 2b. The timing circuits are thus constructed so that a timing signal representing the time period of the T-wave portion of the heartbeat follows each R-S portion of the heartbeat. Thus, regardless of the heartbeat rate or other irregularity in the heartbeat function, the timing period will substantially correspond to the vulnerable T-wave period of the heartbeat. This information is then used to provide protection during application of electrical pulses for transcutaneous nerve stimulation.

Figure 4B:
Figure 4C:
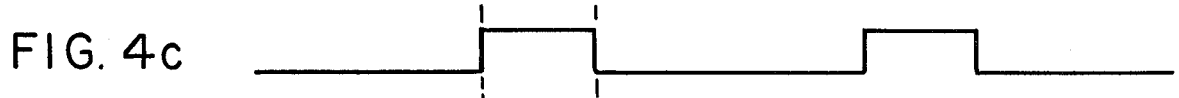
FIG. 4c is a diagram of the inhibiting signal in time relation to the diagrams of FIGS. 4a and 4b.

Referring now to FIG. 3, the system of the present invention is shown to include a transcutaneous nerve stimulator 30 of conventional construction. The output of the transcutaneous nerve stimulator 30 is typically shown in FIG. 4a as a train of repetitive pulses. By appropriate circuitry in the transcutaneous nerve stimulator, these pulses can be varied in amplitude and duration. In addition, the output can be controlled to produce a series of pulses of different frequency or a programmed combination of any of the variables above. The output from the transcutaneous nerve stimulator 30 is coupled to a mixing circuit 34 having a second input which is coupled from the inhibiting circuitry of element 32. The inhibiting circuitry 32 can be either of the circuits of FIG. 2a or FIG. 2b or any other circuitry that may be developed to provide the requisite timing signal for operation of the inventive system. The output of the inhibiting circuitry 32 is generally shown as a timing waveform of FIG. 4c which is initiated during the R-S portion of the heartbeat waveform and lasts for a time period extending beyond the T-wave portion of the heartbeat. The correspondence between the transcutaneous nerve stimulation output, the heartbeat waveform, and the timing circuit can best be seen by reference to FIGS. 4a to 4c wherein the individual waveforms are shown in time relationship to one another.

Figure 4D:
FIG. 4d is a diagram of the waveform produced by the output of the transcutaneous nerve stimulation and inhibiting system of the present invention in time relation to the waveforms of FIG. 4a through FIG. 4c.

The output of the mixing circuit 34 is supplied to the electrodes 36 which are attached to the skin of an individual for application of the transcutaneous nerve stimulation. The function of the mixing circuit 34 is to alter the output of the transcutaneous nerve stimulator 30 as directed by the inhibiting circuit 32. Thus the circuit 34 acts to pass pulses from the transcutaneous nerve stimulator circuit to the applied electrode 36 only during the absence of an inhibiting signal from circuit 32. When signal 32 is present, however, the circuit 34 prevents the output from transcutaneous nerve stimulator 30 from reaching the electrodes 36. This can best be seen by reference to FIG. 4d wherein the timing relationship of the transcutaneous nerve stimulating output pulses is shown in connection with the waveforms of FIG. 4b and FIG. 4c.

as can be seen from the above description, the present invention provides a technique for enabling the application of transcutaneous nerve stimulating pulses to the body of a patient while reducing possible danger to an individual's heart function. The system provides for the sensing of the R-S portion of the heartbeat waveform in order to create a timing pulse which is representative of the time duration of the T-wave portion of the heartbeat. When this timing signal is used in connection with the transcutaneous nerve stimulator, the output pulses of the transcutaneous nerve stimulator can be inhibited during the critical T-wave portion of the heartbeat. This enables the application of higher current waveforms to an individual for treatment of pain and other muscle disorders without the related dangers to the heart. The system can be implemented with simple and inexpensive circuitry yet provide protection in a complex area of treatment. All of these are features which are not shown or taught by the prior art.

While the present invention has been disclosed with reference to specific circuitry and detectors, it is apparent that other configurations of detecting circuitry could be used in conjunction with the transcutaneous nerve stimulator. It is also anticipated that other types of electrical detection circuitry could be used to sense the various portions of the heart waveform in order to provide the requisite timing circuit. Obviously, many other modifications and variations of the invention are possible in light of the above teachings. It is therefore to be understood that within the scope of the appended claims, the invention may be practiced otherwise than as is specifically described.

I claim:

1. A transcutaneous nerve stimulating and inhibiting system comprising:
    means for providing a series of electrical pulses;
    sensing means for detecting a period of the heartbeat of an individual and providing a sensing signal;
    timing means responsive to said sensing signal for providing a timing signal of predetermined duration following detection of said heartbeat period;
    means coupled to receive said pulses and said timing signal for providing an output of said pulses which is suppressed only during the presence of said timing signal; and
    means for coupling said output pulses to the body of an individual.

2. The system of claim 1 wherein said sensing means comprises:
    means for sensing electrical signals representing the heartbeat directly from the body of an individual;
    means for amplifying said sensed electrical signals;
    means for filtering said amplified electrical signals; and
    means for sensing the zero crossing of said filtered electrical signals for providing said sensing signal.

3. The system of claim 1 wherein said sensing means comprises:
    means for detecting the blood pressure of an individual; and
    transducer means responsive to said means for detecting blood pressure for providing said sensing signal upon the detection of a predetermined pressure.

4. The system of claim 1 wherein said sensing means is constructed to detect the R-S transition period of the heartbeat and said timing means is constructed to provide a timing signal having a duration extending from the R-S transition period to a time after the subsequent T-wave portion of the heartbeat.

5. A technique for preventing the application of electrical impulses to an individual receiving transcutaneous nerve stimulation during the T-wave portion of a heartbeat comprising:
    providing a source of electrical pulses for transcutaneous nerve stimulation;

sensing the heartbeat of an individual to detect the R-S transition period of the heartbeat;

providing a timing signal of a predetermined duration following detection of the R-S transition period of the heartbeat and during the T-wave portion of the heartbeat;

combining said timing signal and said electrical pulses to provide an output of said electrical pulses which is suppressed during the presence of the timing signal; and coupling said output pulses to an individual or a transcutaneous nerve stimulation.

6. The process of claim 5 wherein the sensing step comprises:

detecting an electrical signal from the skin of an individual;

amplifying the detected electrical signal;

filtering the amplified electrical signal; and sensing the zero crossing of the filtered electrical signal.

7. The process of claim 5 wherein the sensing step comprises:

detecting the blood pressure of a patient; and converting the sensed detected blood pressure of the patient into an electrical signal corresponding to a particular blood pressure.

8. The process of claim 5 wherein said providing a timing signal step comprises providing a timing signal which has a duration extending from the R-S transition period to a time after the subsequent T-wave portion of the heartbeat.

* * * * *